United States Patent [19]
Howell et al.

[11] Patent Number: 6,007,815
[45] Date of Patent: *Dec. 28, 1999

[54] ANTI-IDIOTYPE VACCINATION AGAINST DISEASES RESULTING FROM PATHOGENIC RESPONSES BY SPECIFIC T CELL POPULATIONS

[75] Inventors: Mark D. Howell, San Diego; Steven W. Brostoff, Carlsbad; Dennis J. Carlo, Rancho Santa Fe, all of Calif.

[73] Assignee: The Immune Response Corporation, Carlsbad, Calif.

[*] Notice: This patent is subject to a terminal disclaimer.

[21] Appl. No.: 08/332,428

[22] Filed: Oct. 31, 1994

Related U.S. Application Data

[63] Continuation of application No. 08/024,787, Mar. 1, 1993, abandoned, which is a continuation of application No. 07/914,642, Jul. 16, 1992, abandoned, which is a continuation of application No. 07/382,086, Jul. 18, 1989, abandoned, and a continuation-in-part of application No. 07/326,314, Mar. 21, 1989, abandoned.

[51] Int. Cl.$^6$ .......................... A61K 39/395; C07K 16/42
[52] U.S. Cl. ..................................... 424/131.1; 530/387.2; 530/395
[58] Field of Search ..................................... 530/300, 350, 530/395, 868, 388.75, 389.6, 387.2; 424/184.1, 193.1, 131.1, 143.1; 514/2, 8

[56] References Cited

U.S. PATENT DOCUMENTS

| | | | |
|---|---|---|---|
| 4,886,743 | 12/1989 | Hood et al. | 435/5 |
| 5,612,035 | 3/1997 | Howell et al. | 424/185.1 |

FOREIGN PATENT DOCUMENTS

| | | | |
|---|---|---|---|
| 86/06413 | 11/1986 | WIPO | C12Q 1/68 |
| WO-A-86/ 06413 | 11/1986 | WIPO | C12Q 1/68 |
| WO 91/01133 | 2/1991 | WIPO | A67K 31/00 |

OTHER PUBLICATIONS

Makoto Owhashi and Ellen Heber–Katz, Protection From Experimental Allergic Encephalomyelitis Conferred by a Monoclonal Antibody Directed Against a Shared Idiotype on Rat T Cell Receptors Specific for Myelin Basic Protein, J. Exp. Med. 168:2153–2164 (1988).

Yanagi et al., A Human T–cell–specific cDNA Clone Encodes a Protein Having Extensive Homology to Immunoglobulin Chains, Nature 308:145–149 (1984).

Biddison et al., The Germline Repertoire of T–cell Receptor Beta–chain Genes in Patients with Multiple Sclerosis, Research Immunology 140:212–215 (1989).

Ross et al., Antibodies to Synthetic Peptides Corresponding to Variable–region First–framework Segments of T–cell Receptors, Immunol. Res. 8:81–97 (1989).

Urban et al., Restricted use of T cell receptor V genes in murine autoimmune encephalomyelitis raises possibilities for antibody therapy. Cell 54:577–592 (1988).

Lider et al., Anti–idiotypic network induced by T cell vaccination against experimental autoimmune encephalomyelitis. Science 239:181–183 (1988).

Sun et al., Suppression of experimentally induced autoimmune encephalomyelitis by cytolytic T–T cell interactions. Nature 332:843–845 (1988).

Offner et al., Lymphocyte vaccination against experimental autoimmune encephalomyelitis: evaluation of vaccination protocols. J. Neuroimmunol. 21:13–22 (1989).

Choi et al., Interaction of *Staphylococcus aureus* toxin "superantigens" with human T cells. Proc. Natl. Acad. Sci. USA 86:8941–8945 (1989).

White et al., The Vβ–specific superantigen staphylococcal enterotoxin B: stimulation of mature T cells and clonal deletion in neonatal mice. Cell 56:27–35 (1989).

Pullen et al., Identification of the region of T cell receptor β chain that interacts with the self–superantigen Mls–1$^a$. Cell 61:1365–1374 (1990).

Janeway, C., Self superantigens? Cell 63:659–661 (1990).

Marrack and Kappler, The staphylococcal enterotoxins and their relatives. Science 248:705–711 (1990).

Schluter et al., Antibodies to synthetic joining segment peptide of the T–cell receptor β–chain: serological cross–reaction between products of T–cell receptor genes, antigen binding T–cell receptors and immunoglobulns. Chem. Abstracts 105(1):464, abstract no. 4767q (1986).

Howell et al., Vaccination against experimental allergic encephalomyelitis with T cell receptor peptides. Science 246(4930):668–670 (1989).

Vandenbark et al., Immunization with a synthetic T–cell receptor V–region peptide protects against experimental autoimmune encephalomyelitis. Letters to Nature 341:541–544 (1989).

Patten et al., Structure, expression and divergence of T–cell receptor β–chain variable regions, Nature 312:40–46 (1984).

Ben–Nun et al., Vaccination against autoimmune encephalomyelitis with T–lymphocyte line cells reactive against myelin basic protein. Nature 292:60–61 (1981).

(List continued on next page.)

Primary Examiner—Thomas M. Cunningham
Attorney, Agent, or Firm—Campbell & Flores LLP

[57] ABSTRACT

The present invention provides vaccines and a means of vaccinating a host so as to prevent or control specific T cell mediated pathologies. The vaccine is composed of anti-idiotypic antibodies which are internal images of a segment of the T cell receptor (TCR) present on the surface of the pathogenic T cells. The vaccine is administered to the host in a manner that induces an immune response directed against the TCR of pathologic T cell. This immune response down regulates or deletes the pathogenic T cells, thus ablating the disease pathogenesis. Means of determining an appropriate amino acid sequence for such a vaccine are also provided.

17 Claims, No Drawings

OTHER PUBLICATIONS

Acha–Orbea et al., Limited heterogeneity of T cell receptors from lymphocytes mediating autoimmune encephalomyelitis allows specific immune intervention. *Cell* 54:263–273 (1988).

Burns et al., Both rat and mouse T cell receptors specific for the encephalitogenic determinant of myelin basic protein use similar V α and V β chain genes even though the major histocompatibility complex of encephalitogenic determinants being recognized are different. *J. Exp. Med.* 169:27–39 (1989).

Chluba et al., T cell receptor β chain usage in myelin basic protein–specific rat T lymphocytes. *Eur. J. Immunol.* 19:279–284 (1989).

Wucherpfennig et al., Shared human T cell receptor Vβ usage to immunodominant regions of myelin basic protein. *Science* 248:1016–1019 (1990).

Kimura et al., Sequences and repertoire of the human T cell receptor α and β chain variable region genes in thymocytes. *Eur. J. Immunol.* 17:375–383 (1987).

Sedgwick, J., Long–term depletion of CD8$^+$ T cells in vivo in the rat: no observed role for CD8$^+$ (cytotoxic/ suppressor) cells in the immunoregulation of experimental allergic encephalomyelitis. *Eur. J. Immunol.* 18:495–502 (1988).

Zamvil et al., Predominant expression of a T cell receptor $V_\beta$ gene subfamily in autoimmune encephalomyelitis, *J. Exp. Med.* 167:1586–1596 (1988).

Clark et al., "Shared T–cell Receptor Gene Usage in Experimental Allergic Neuritis and Encephalomyelitis" *Ann. Neurol.* 31:587–592 (1992).

Sellins et al., "Limited T Cell Receptor β–Chain Usage in the Sperm Whale Myoglobin 110–121/Eαd Aβd Response by H–2d Congenic Mouse Strains" *J. Immunol.* 149:2323–2327 (1992).

Lahesmaa et al., "Preferential Usage of T Cell Antigen Receptor V Region Gene Segment Vβ5.1 by Borrelia burgdorferi Antigen–Reactive T Cell Clones Isolated from a Patient with Lyme Disease" *J. Immunol.* 150:4125–4135 (1993).

Abe et al., "Selective expansion of T cells expressing T–cell receptor variable regions Vβ2 and Vβ8 in Kawasaki disease" *Proc. Natl. Acad. Sci. U.S.A.* 89:4066–4070 (1992).

Gaur et al., "Requirement for CD8+ Cells in T Cell Receptor Peptide–Induced Clonal Unresponsiveness" *Science* 259:91–94 (1993).

Gregorian et al., "Immune Regulation by T–Cell Receptor (TCR) V Region Peptide in Experimental Autoimmune Neuritis" *FASEB J.* 6:A1685 (1992).

Kawano et al., "Trials of Vaccination Against Experimental Autoimmune Uveoretinitis with a T–cell Receptor Peptide" *Cancer Eye Research* 10:789–795 (1991).

Welch et al., "Regulation of Experimental Allergic Encephalomyelitis" *J. Immunol.* 125:186–189 (1980).

Infante et al., "Preferential Use of a T Cell Receptor Vβ Gene By Acetylcholine Receptor Reactive T Cells From Myasthenia Gravis–Susceptible Mice" *J. Immunol.* 148:3385–3390 (1992).

Paliard et al., "Evidence for the Effects of a Superantigen in Rheumatoid Arthritis" *Science* 253:325–329 (1991).

Howell et al., "Limited T–cell receptor β–chain heterogeneity among interleukin 2 receptor–positive synovial T cells suggests a role for superantigen in rheumatoid arthritis" *Proc. Natl. Acad. Sci. (U.S.A.)* 88:10921–10925 (1991).

Grunewald et al., "Abnormal T–Cell Expansion and V–Gene Usage in Myasthenia Gravis Patients" *Scand. J. Immunol.* 34:161–168 (1992).

Grunewald et al., "Restricted Vα2.3 gene usage by CD4+ T lymphocytes in bronchoaiveolar lavage fluid from sarcoidosis pateints correlates with HLA–DR3" *Eur. J. Immunol.* 22:129–135 (1992).

Lee et al., "Common T–cell Receptor Usage in Oligoclonal Lymphocytes derived from Cerebrospinal Fluid and Blood of Patients with Multiple Sclerosis" *Ann. Neurol.* 29:33–40 (1991).

Posnett et al., "T Cell Antigen Receptor V Gene Usage" *J. Clin. Invest.* 85:1770–1776 (1990).

Edouard et al., "Evidence for a preferential Vβ usage by the T cells which adoptively transfer diabetes in NOD mice" *Eur. J. Immunol.* 23:727–733 (1993).

Smith et al., "Acute Infectious Mononucleosis Stimulates the Selective Expression/Expansion of Vβ6.1–3 and Vβ7 T Cells" *Blood* 81:1521–1526 (1993).

ANTI-IDIOTYPE VACCINATION AGAINST DISEASES RESULTING FROM PATHOGENIC RESPONSES BY SPECIFIC T CELL POPULATIONS

This application is a continuation of application Ser. No. 08/024,787 filed Mar. 1, 1993 abandoned; which is a continuation of U.S. Ser. No. 07/914,642 filed Jul. 16, 1992 (now abandoned); which is a continuation of U.S. Ser. No. 07/382,086 filed Jul. 18, 1989 abandoned; and a continuation-in-part of U.S. Ser. No. 07/326,314 filed Mar. 21, 1989 abandoned.

BACKGROUND OF THE INVENTION

This invention relates to the immune system and, more specifically, to methods of modifying pathological immune responses.

Higher organisms are characterized by an immune system which protects them against invasion by potentially deleterious substances or microorganisms. When a substance, termed an antigen, enters the body, and is recognized as foreign, the immune system mounts both an antibody-mediated response and a cell-mediated response. Cells of the immune system, termed B lymphocytes or B cells, produce antibodies which specifically recognize and bind to the foreign substance. Other lymphocytes, termed T lymphocytes or T cells, both effect and regulate the cell-mediated response resulting eventually in the elimination of the antigen.

A variety of T cells are involved in the cell-mediated response. Some induce particular B cell clones to proliferate and produce antibodies specific for the antigen. Others recognize and destroy cells presenting foreign antigens on their surfaces. Certain T cells regulate the response by either stimulating or suppressing other cells.

While the normal immune system is closely regulated, aberrations in immune response are not uncommon. In some instances, the immune system functions inappropriately and reacts to a component of the host as if it were, in fact, foreign. Such a response results in an autoimmune disease, in which the host's immune system attacks the host's own tissue. T cells, as the primary regulators of the immune system, directly or indirectly effect such autoimmune pathologies.

Numerous diseases are believed to result from autoimmune mechanisms. Prominent among these are rheumatoid arthritis, systemic lupus erythematosus, multiple sclerosis, Type I diabetes, myasthenia gravis and pemphigus vulgaris. Autoimmune diseases affect millions of individuals worldwide and the cost of these diseases, in terms of actual treatment and expenditures and lost productivity, is measured in billions of dollars annually. At present, there are no known effective treatment for such autoimmune pathologies. Usually, only the symptoms can be treated, while the disease continues to progress, often resulting in severe debilitation or death.

In other instances, lymphocytes replicate inappropriately and without control. Such replication results in a cancerous condition known as a lymphoma. Where the unregulated lymphocytes are of the T cell type, the tumors are termed T cell lymphomas. As with other malignancies, T cell lymphomas are difficult to treat effectively.

Thus there exists a long-felt need for an effective means of curing or ameliorating T cell mediated pathologies. Such a treatment should ideally control the inappropriate T cell response, rather than merely reducing the symptoms. The present invention satisfies this need and provides related advantages as well.

SUMMARY OF THE INVENTION

The present invention provides vaccines and a means of vaccinating a mammal so as to prevent or control a specific T cell mediated pathologies. The vaccine is composed of a T cell receptor (TCR) or a fragment thereof corresponding to a TCR present on the surface of T cells mediating the pathology. Alternatively, the vaccine can be a peptide corresponding to sequences of TCRs characteristic of the T cells mediating said pathology, or anti-idiotypic antibodies which are internal images of the peptides.

Moreover, the invention provides vaccines for treating the unregulated replication of T cells. The vaccine is composed of a TCR or a fragment thereof corresponding to TCR present on the surface of the unregulated T cells. Alternatively, the vaccine can be a peptide corresponding to sequences of TCRs characteristic of the unregulated replicating T cells.

Means of determining appropriate amino acid sequences for such vaccines are also provided. The vaccine is administered to the mammal in a manner that induces an immune response directed against the TCR of T cells mediating the pathology. This immune response down regulates or deletes the pathogenic T cells, thus ablating the disease pathogenesis.

DETAILED DESCRIPTION OF THE INVENTION

The invention relates to vaccines and their use for preventing or ameliorating T cell-mediated pathologies, such as autoimmune diseases and T cell lymphomas. Vaccination provides a specific and sustained treatment which avoids problems associated with other potential avenues of therapy.

As used herein, the term "T cell-mediated pathology" refers to any condition in which an inappropriate T cell response is a component of the pathology. The term is intended to include both diseases directly mediated by T cells and those, such as myasthenia gravis, which are characterized primarily by damage resulting from antibody binding, but also reflect an inappropriate T cell response which contributes to the production of those antibodies.

As used herein when referring to the relationship between peptides of the invention and sequences of TCRs "corresponding to" means that the peptide has an amino acid sequence which is sufficiently homologous to the TCR sequence to stimulate an effective regulatory response need not be identical to the TCR sequence, however, as shown in Examples II and III.

The immune system is the primary biological defense of the host (self) against potentially pernicious agents (non-self). These pernicious agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

The principal manifestations of an antigen-specific immune response are humoral immunity (antibody mediated) and cellular immunity (cell mediated). Each of these immunological mechanisms are initiated through the activation of helper (CD4+) T cells. These CD4+ T cells in turn stimulate B cells, primed for antibody synthesis by antigen binding, to proliferate and secrete antibody. This secreted antibody binds to the antigen and facilitates its destruction by other immune mechanisms. Similarly, CD4+ T cells provide stimulatory signals to cytotoxic (CD8+) T cells which recognize and destroy cellular targets (for example, virus infected cells of the host). Thus, the activation of CD4+ T cells is crucial in any attempt to selectively modify immunological function.

T cells owe their antigen specificity to the T cell receptor (TCR) which is expressed on the cell surface. The TCR is a heterodimeric glycoprotein, composed of two polypeptide chains, each with a molecular weight of approximately 45 kD. Two forms of the TCR have been identified. One is composed of an alpha chain and a beta chain, while the second consists of a gamma chain and a delta chain. Each of these four TCR polypeptide chains is encoded by a distinct genetic locus containing multiple discontinuous gene segments. These include variable (V) region gene segments, joining (J) region gene segments and constant (C) region gene segments. Beta and delta chains contain an additional element termed the diversity (D) gene segment. (Since D segments and elements are found in only some of the TCR genetic loci, and polypeptides, further references herein to D segments and elements will be in parentheses to indicate the inclusion of these regions only in the appropriate TCR chains. Thus V(D)J refers either to VDJ sequences of chains which have a D region or refers to VJ sequences of chains lacking D regions.)

During lymphocyte maturation, single V, (D) and J gene segments are rearranged to form a functional gene that determines the amino acid sequence of the TCR expressed by that cell. Since the pool of V, (D) and J genes which may be rearranged is multi-membered and since individual members of these pools may be rearranged in virtually any combination, the complete TCR repertoire is highly diverse and capable of specifically recognizing and binding the vast array of antigens to which an organism may be exposed. However, a particular T cell will have only one TCR molecule and that TCR molecule, to a large degree if not singly, determines the antigen specificity of that T cell.

T-Cell Pathologies of Autoimmune Etiology

Animal models have contributed significantly to our understanding of the immunological mechanisms of autoimmune disease. One such animal model, experimental allergic encephalomyelitis (EAE), is an autoimmune disease of the central nervous system that can be induced in mice and rats by immunization with myelin basic protein (MBP). The disease is characterized clinically by paralysis and mild wasting and histologically by a perivascular mononuclear cell infiltration of the central nervous system parenchyma. The disease pathogenesis is mediated by T cells with specificity for MBP. Multiple clones of MBP-specific T cells have been isolated from animals suffering from EAE and have been propagated in continuous culture. After in vitro stimulation with MBP, these T cell clones rapidly induce EAE when adoptively transferred to healthy hosts. Importantly, these EAE-inducing T cells are specific, not only for the same antigen (MBP), but also usually for a single epitope on that antigen. These observations indicate that discrete populations of autoaggressive T cells are responsible for the pathogenesis of EAE.

Analysis of the TCRs of EAE-inducing T cells has revealed restricted heterogeneity in the structure of these disease-associated receptors. In one analysis of 33 MBP-reactive T cells, only two alpha chain V region gene segments and a single alpha chain J region gene segment were utilized. Similar restriction of beta chain TCR gene usage was also observed in this T cell population. Only two beta chain V region segments and two J region gene segments were found. More importantly, approximately eighty percent of the T cell clones had identical amino acid sequences across the region of beta chain V-D-J joining. These findings confirm the notion of common TCR structure among T cells with similar antigen specificities and indicate that the TCR is an effective target for immunotherapeutic strategies aimed at eliminating the pathogenesis of EAE.

Various attempts have been made to exploit the antigen specificity of the autoaggressive T cells in devising treatment strategies for EAE. For example, passive administration of monoclonal antibodies specific for TCRs present on EAE-inducing T cells has been employed. In the mouse model of EAE, infusion of a monoclonal antibody specific for $V_\beta 8$, the major beta chain V region gene used by MBP-specific T cells, reduced the susceptibility of mice to subsequent EAE induction (Acha-Orbea et al., Cell 54:263–273 (1988) and Urban et al., Cell 54:577–592 (1988)). Similar protection has been demonstrated in rat EAE with a monoclonal antibody reactive with an unidentified idiotypic determinant of the TCR on MBP specific T cells (Burns et al., J. Exp. Med. 169:27–39 (1989)). While passive antibody therapy appears to have some ameliorative effect on EAE susceptibility, it is fraught with potential problems. The protection afforded is transient, thus requiring repeated administration of the antibody. Multiple infusions of antibody increases the chances that the host will mount an immune response to the administered antibody, particularly if it is raised in a xenogeneic animal. Further an antibody response to a pathogenic T cell clone represents only one element in the complete immune response and neglects the potential contributions of cellular immunity in resolving the autoreactivity.

The role of cellular immunity in reducing the activity of autoaggressive T cells in EAE has been examined and potential therapies suggested. In a manner similar to the passive antibody approach, regulatory T cells have been derived ex vivo and readministered for immunotherapy. For example, Sun et al., Nature, 332:843–845 (1988), have recently isolated a CD8+ T cell clone from convalescing rats in whom EAE had been induced by adoptive transfer of an MBP-specific CD4+ T cell line. This CD8+ T cell clone displayed cytolytic activity in vitro for the CD4+ T cell used to induce disease. Moreover, adoptive transfer of this CTL clone reduced the susceptibility of recipient rats to subsequent challenge with MBP. Lider, et al., (Science, 239:181–183 (1988)) have also isolated a CD8+ T cell clone with suppressive activity for EAE-inducing T cells. This CD8+ clone was isolated from rats vaccinated with attenuated disease-inducing T cell clones and, though it showed no cytolytic activity in vitro, it could suppress MBP-driven proliferation of EAE-inducing T cells. Although these studies indicate that the CD8+ T cells could downregulate EAE, it is hard to reconcile a major role for these selected CD8+ CTLs in the long-term resistance of recovered rats since Sedgwick, et al., (Eur. J. Immunol., 18:495–502 (1988)) have clearly shown that depletion of CD8+ cells with monoclonal antibodies does not affect the disease process or recovery.

In the experiments of Sun et al., and Lider et al., described above, the administration of extant derived regulatory T cells overcomes the major obstacle of passive antibody therapy; it permits a regulatory response in vivo of prolonged duration. However, it requires in vitro cultivation with attenuated disease-inducing T cells to develop clones of such regulatory T cells, a costly and labor intensive process. Further, in an outbred population such as humans, MHC non-identity among individuals makes this a highly individualized therapeutic strategy. Regulatory clones need to be derived for each individual patient and then re-administered only to that patient to avoid potential graft versus host reactions.

Direct vaccination with attenuated disease-inducing T cell clones also has been employed as a therapy for EAE. MBP-specific T cells, capable of transferring disease, have been attenuated by gamma irradiation or chemical fixation and used to vaccinate naive rats. In some cases, vaccinated animals exhibited resistance to subsequent attempts at EAE induction (Lider et al., supra; see Cohen and Weiner, Immunol. Today 9:332–335 (1988) for review). The effectiveness of such vaccinations, however, is inconsistent and the degree of protection is highly variable. T cells contain a multitude of different antigens which induce an immune response when the whole T cell is administered as a vaccine. This phenomenon has been demonstrated by Offner et al., (J. Neuroimmunol., 21:13–22 (1989)), who showed that immunization with whole T cells increased the delayed type hypersensitivity (DTH) response as measured by ear swelling to those T cells in an incremental manner as the number of vaccinations increased. However, positive DTH responses were found in both protected and non-protected animals. Rats responded similarly to both the vaccinating encephalitogenic T cells and control T cells. Conversely, vaccination with PPD-specific T cells from a PPD-specific T cell line induced DTH to the vaccinating cells as well as to an encephalitogenic clone even though no protection was observed. The similar response of vaccinated rats to both disease-inducing and control cells, as quantified by delayed-type hypersensitivity (a measure of cell-mediated immunity), indicates that numerous antigens on these T cells are inducing immune responses. Thus, vaccination with attenuated disease-inducing T cells suffers from a lack of specificity for the protective antigen on the surface of that T cell, as well as, variable induction of immunity to that antigen. As a candidate for the treatment of human disease, vaccination with attenuated T cells is plagued by the same labor intensiveness and need for individualized therapies as noted above for infusion of CD8+ cells.

The present invention provides an effective method of immunotherapy for T cell mediated pathologies, including autoimmune diseases, which avoids many of the problems associated with the previously suggested methods of treatment. By vaccinating, rather than passively administering heterologous antibodies, the host's own immune system is mobilized to suppress the autoaggressive T cells. Thus, the suppression is persistent and may involve any and all immunological mechanisms in effecting that suppression. This multi-faceted response is more effective than the uni-dimensional antibodies or extant-derived regulatory T cell clones.

As they relate to autoimmune disease, the vaccines of the present invention comprise TCRs of T cells that mediate autoimmune diseases. The vaccines can be whole TCRs substantially purified from T cell clones, individual T cell receptor chains (for example, alpha, beta, etc.) or portions of such chains, either alone or in combination. The vaccine can be homogenous, for example, a single peptide, or can be composed of more than one peptide, each of which corresponds to a portion of the TCR. By "substantially pure" it is meant that the TCR is substantially free of other biochemical moieties with which it is normally associated in nature. Alternatively, the vaccines comprise peptides of varying lengths corresponding to the TCR or portions thereof. The peptides can be produced synthetically or recombinantly, by means well known to those skilled in the art. Preferably, the peptide vaccines correspond to regions of the TCR which distinguish that TCR from other nonpathogenic TCRs. Such specific regions are preferably located within the V region(s) of the respective TCR polypeptide chains. Most preferably, the peptide corresponds to a short sequence spanning the V(D)J junction, thus restricting the immune response solely to those T cells bearing this single determinant.

Alternatively, the vaccines can comprise anti-idiotypic antibodies which are internal images of the peptides described above. Methods of making, selecting and administering such anti-idiotype vaccines are well known in the art. See for example, Eichmann, et al, CRC Critical Reviews in Immunology 7:193–227 (1987), which is incorporated herein by reference.

The vaccines are administered to a host exhibiting or at risk of exhibiting an autoimmune response. Definite clinical active autoaggressive activity such as a lesion in the case of pemphigus vulgaris, CNS in the case of multiple sclerosis or myasthenia gravis or synovial fluid or tissue in the case of rheumatoid arthritis. The TCR genes from these autoaggressive T cells are then sequenced. Polypeptides corresponding to TCRs or portions thereof that are selectively represented among disease inducing T cells (relative to non-pathogenic T cells) can then be selected as vaccines, and made and used as described above.

T Cell Pathologies of Malignant Etiology

To illustrate the utility of TCR vaccination, autoimmune disease has been discussed. However, T cell lymphoma is another T cell pathology which would be amenable to this type of treatment. Application of this technology in the treatment of T lymphoma would be conducted in virtually identical fashion. In one important respect, however, this technology is more readily applied to T cell proliferative disease since the isolation of the pathogenic T cells is more easily accomplished. Once the clones are isolated the technology is applied in the manner described above. Specifically, the TCR genes of the T lymphoma are sequenced, appropriate regions of those TCRs are identified and used as vaccines. The vaccines can comprise single or multiple peptides, and can be administered in formulations with or without adjuvants by conventional means.

The following examples are intended to illustrate but not limit the invention.

EXAMPLE I

Rat Model of EAE

Female Lewis rats, (Charles River Laboratories, Raleigh-Durham, N.C.), were immunized in each hind foot pad with 50 µg of guinea pig myelin basic protein emulsified in complete Freund's adjuvant. The first signs of disease were typically observed 9 to 11 days post-immunization. Disease severity was scored on a three point scale as follows: 1=limp tail; 2=hind leg weakness; 3=hind leg paralysis. Following a disease course of approximately four to six days, most rats spontaneously recovered and were refractory to subsequent EAE induction.

EXAMPLE II

Selection and Preparation of Vaccines

Vaccinations were conducted with a T cell receptor peptide whose sequence was deduced from the DNA sequence of a T cell receptor beta chain gene predominating among EAE-inducing T cells of SJ/L mice. The DNA sequence was that reported by Urban, et al., supra, which is incorporated herein by reference. A nine amino acid peptide, having the sequence of VDJ junction of the TCR beta chain of the mouse, was synthesized by methods known to those skilled in the art. The sequence of this peptide is: SGDAGGGYE. (Amino acids are represented by the conventional single letter codes.) The equivalent sequence in the rat has been reported to be: SSD-SSNTE (Burns et al., J. Exp. Med. 169:27–39 (1989)). The peptide was desalted by Sephadex G-25 (Pharmacia Fine Chemicals, Piscataway, N.J.) column chromatography in 0.1 M acetic acid and the solvent was subsequently removed by two cycles of lyophilization. A portion of the peptide was conjugated to keyhole limpet hemocyanin (KLH) with glutaraldehyde at a ratio of 7.5 mgs of peptide per mg of KLH. The resulting conjugate was dialyzed against phosphate buffered saline (PBS).

EXAMPLE III

Vaccination Against EAE

Vaccines used in these studies consisted of free VDJ peptide and also of VDJ peptide conjugated to KLH. These were dissolved in PBS and were emulsified with equal volumes of either (1) incomplete Freund's adjuvant (IFA) or (2) complete Freund's adjuvant (CFA), made by suspending 10 mg/ml heat-killed desiccated Mycobacterium tuberculosis H37ra (Difco Laboratories, Detroit, Mich.) in IFA. Emulsions were administered to 8–10 week old female Lewis rats in a final volume of 100 microliters per rat (50 microliters in each of the hind footpads). 5 μg of unconjugated VDJ peptide were administered per rat. KLH-VDJ conjugate was administered at a dose equivalent to 10 μg of KLH per rat. Twenty-nine days later each rat was challenged with 50 μg of guinea pig myelin basic protein in complete Freund's adjuvant in the front footpads. Animals were monitored daily beginning at day 9 for clinical signs of EAE and were scored as described above. The results are presented in Table I. As can be seen, not only was there a reduced incidence of the disease in the vaccinated individuals, but in those which did contract the disease, the severity of the disease was reduced and/or the onset was delayed. The extent of protection varied with the vaccine formulation, those including CFA as the adjuvant demonstrating the greatest degree of protection.

TABLE I

| Animal No. | Vaccination (Adjuvant) | Days After Challenge | | | | | | | | |
|---|---|---|---|---|---|---|---|---|---|---|
| | | 10 | 11 | 12 | 13 | 14 | 15 | 16 | 17 | 18 |
| 1 | VDJ (IFA) | — | — | 2 | 3 | 3 | 3 | — | — | — |
| 2 | " | — | — | 1 | 3 | 3 | 3 | 2 | — | — |
| 3 | " | — | — | — | 3 | 3 | 3 | 2 | — | — |
| 4 | VDJ (CFA) | — | — | — | — | 1 | 1 | 1 | — | — |
| 5 | " | — | — | — | — | — | — | — | — | — |
| 6 | " | — | — | — | 1 | 3 | 3 | 3 | 2 | — |
| 7 | KLH-VDJ (CFA) | — | — | — | 1 | 3 | 2 | — | — | — |
| 8 | " | — | — | — | — | 1 | 1 | 1 | 1 | — |
| 9 | " | — | — | — | — | — | — | — | — | — |
| 10 | KLH-VDJ (IFA) | — | 1 | 3 | 3 | 2 | 2 | 1 | — | — |
| 11 | " | — | — | 3 | 3 | 3 | 3 | 3 | 2 | — |
| 12 | " | — | — | 1 | 3 | 3 | 3 | 3 | — | — |
| 13 | NONE | 1 | 3 | 3 | 3 | 3 | 1 | — | — | — |
| 14 | " | — | 1 | 3 | 3 | 3 | 1 | — | — | — |
| 15 | " | 1 | 3 | 3 | 3 | 1 | — | — | — | — |

Scoring:
— no signs
1) limp tail
2) hind leg weakness
3) hind leg paralysis

Although the invention has been described with reference to the presently-preferred embodiment, it should be understood that various modifications can be made without departing from the spirit of the invention. Accordingly, the invention is limited only by the following claims.

We claim:

1. A composition for reducing the severity of a T cell mediated pathology characterized by restricted T cell receptor gene use, comprising an anti-idiotypic antibody which is an internal image of an amino acid sequence of a T cell receptor (TCR) present on the surface of an autoaggressive T cells mediating said pathology and a pharmaceutically acceptable medium, wherein said anti-idiotypic antibody induces an immune response against said autoaggressive T cells that reduces the severity of said pathology.

2. The composition of claim 1 wherein said anti-idiotypic antibody corresponds to a fragment of said amino acid sequence of said T cell receptor.

3. The composition of claim 2 wherein said fragment comprises a V(D)J junctional sequence.

4. The composition of claim 1 further comprising an adjuvant.

5. The composition of claim 1 or 2, wherein said composition comprises anti-idiotype antibodies which are internal images of amino acid sequences of more than one T cell receptor or a fragment thereof or which are internal images of amino acid sequences corresponding to one or more different fragments of the same said T cell receptor.

6. A method of reducing the severity of a T cell mediated pathology characterized by restricted T cell receptor gene use of an individual exhibiting or at risk of exhibiting a T cell-mediated pathology, comprising administering an immunologically effective amount of the composition of claim 1 or 2.

7. The method of claim 6 wherein said composition is conjugated to a carrier.

8. The method of claim 6 wherein said composition is administered more than once.

9. The method of claim 6 wherein said composition is administered in formulation including an adjuvant.

10. A composition for reducing the severity of a T cell proliferative disease mediated by unregulated T cell clonal replication characterized by restricted T cell receptor gene use, comprising an anti-idiotypic antibody which is an internal image of amino acid sequence of a T cell receptor (TCR) present on the surface of said replicating T cell clones, wherein said anti-idiotypic antibody induces an immune response against said replicating T cell clones that reduces the severity of said disease.

11. The composition of claim 10 wherein said anti-idiotypic antibody corresponds to a fragment of said amino acid sequence of said T cell receptor.

12. The composition of claim 11 wherein said fragment comprises a V(D)J junctional sequence.

13. The composition of claim 10 further comprising an adjuvant.

14. A method of reducing the severity of a T cell mediated pathology characterized by restricted T cell receptor gene use of an individual exhibiting or at risk of exhibiting a T cell-mediated pathology, comprising administering the composition of claim 10.

15. The method of claim 14 wherein said composition is conjugated to a carrier.

16. The method of claim 14 wherein said composition is administered more than once.

17. The method of claim 14 wherein said composition is administered in a formulation including an adjuvant.

* * * * *